United States Patent [19]

Aigami et al.

[11] 4,229,375
[45] Oct. 21, 1980

[54] 1-AMINOMETHYLTRICYCLO[4.3.1.1$^{2,5}$]UNDECANE AND ACID-ADDITION SALTS THEREOF

[75] Inventors: Koji Aigami; Yoshiaki Inamoto; Motoyoshi Ohsugi; Yoshiaki Fujikura, all of Wakayama; Naotake Takaishi, Sakura, all of Japan

[73] Assignee: Kao Soap Company, Limited, Tokyo, Japan

[21] Appl. No.: 15,916

[22] Filed: Feb. 28, 1979

Related U.S. Application Data

[63] Continuation-in-part of Ser. No. 920,967, Jun. 30, 1978, abandoned.

[30] Foreign Application Priority Data

Jul. 4, 1977 [JP] Japan .................................. 52-79752

[51] Int. Cl.$^2$ .............................................. C07C 83/00
[52] U.S. Cl. .................................. 260/563 P; 424/325
[58] Field of Search ..................................... 260/563 P

[56] References Cited

U.S. PATENT DOCUMENTS

| | | | |
|---|---|---|---|
| 3,397,233 | 8/1968 | Cairns | 260/563 P |
| 3,729,513 | 4/1973 | Berezin | 260/563 P X |

*Primary Examiner*—Paul F. Shaver
*Attorney, Agent, or Firm*—Oblon, Fisher, Spivak, McClelland & Maier

[57] ABSTRACT

1-Aminomethyltricyclo[4.3.1.1$^{2,5}$]undecane having the formula (I) and acid-addition salts thereof possess an excellent inhibitory effect on the growth of viruses even at a low concentration.

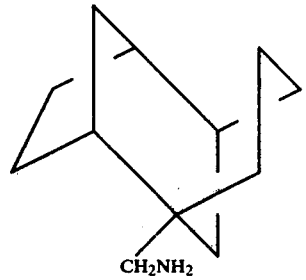

2 Claims, No Drawings

1-AMINOMETHYLTRICYCLO[4.3.1.1$^{2,5}$]UNDECANE AND ACID-ADDITION SALTS THEREOF

REFERENCE TO RELATED APPLICATION

This application is a continuation-in-part application of Applicants' copending application Ser. No. 920,967 filed June 30, 1978, now abandoned.

BACKGROUND OF THE INVENTION

1. Field of the Invention

This invention relates to novel tricycloundecylamines and acid-addition salts thereof, and more particularly, to 1-aminomethyltricyclo[4.3.1.1$^{2,5}$]undercane represented by the formula (I) and acid-addition salts thereof.

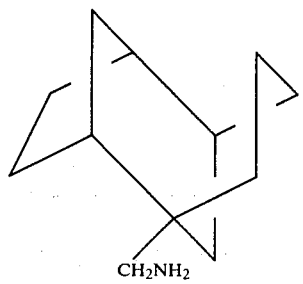

(I)

2. Description of the Prior Art

The basic skeleton of the compound of the formula (I), that is, tricyclo[4.3.1.1$^{2,5}$]undecane, was first reported as an isomerization intermediate by N. Takaishi et al [N. Takaishi et al, J. Chem. Soc., Perkin I, 789 (1975)]. In fact, the present inventers have disclosed several derivatives of tricyclo[4.3.2.1$^{2,5}$]undecane such as 1-hydroxytricyclo[4.3.2.1$^{2,5}$]undecane (Japanese Patent Publication No. 1978-46948), 1-halogenotricyclo[4.3.2.1$^{2,5}$]undecane (Japanese Patent Publication No. 1978-46949), 1-amino[4.3.2.1$^{2,5}$]undecane (Japanese Patent Publication No. 1978-50150) and 1-acetylaminotricyclo[4.3.2.1$^{2,5}$]undecane (Japanese Patent Publications Nos. 1978-46950 and 1978-63362), but the compound of the formula (I) has not been discovered nor synthesized.

SUMMARY OF THE INVENTION

The compound of the formula (I) is structurally analogous to 1-aminotricyclo[4.3.1.1$^{2,5}$]undecane which has already been disclosed by the present inventors (Japanese Patent Publication No. 1978-50150). The compound according to the invention exerts an inhibitory effect on the growth of viruses at a lower concentration than the earlier compound, 1-aminotricyclo[4.3.1.1$^{2,5}$]undecane. Particularly, the compound of the formula (I) possesses an excellent inhibitory effect on the growth of Newcastle disease virus among Paramyxoviruses belonging to RNA viruses in chick embryo fibroblasts; that is, the compound of the formula (I) can inhibit the multiplication of viruses at about 1/6 and ½ the concentrations of adamantylamine hydrochloride, which is well known to be an anti-influenza viral agent, and 1-aminotricyclo[4.3.1.1$^{2,5}$]undecane, respectively. Thus, the compound of the formula (I) is very useful as an ingredient of a medicine for human beings or a drug for animals.

DETAILED DESCRIPTION OF THE PREFERRED EMBODIMENTS

The compound of the present invention represented by the formula (I) can be synthesized, for instance, by reducing 1-aminocarbonyltricyclo[4.3.1.1$^{2,5}$]undecane of the formula (II) or 1-cyanotricyclo[4.3.1.1$^{2,5}$]undecane of the formula (III).

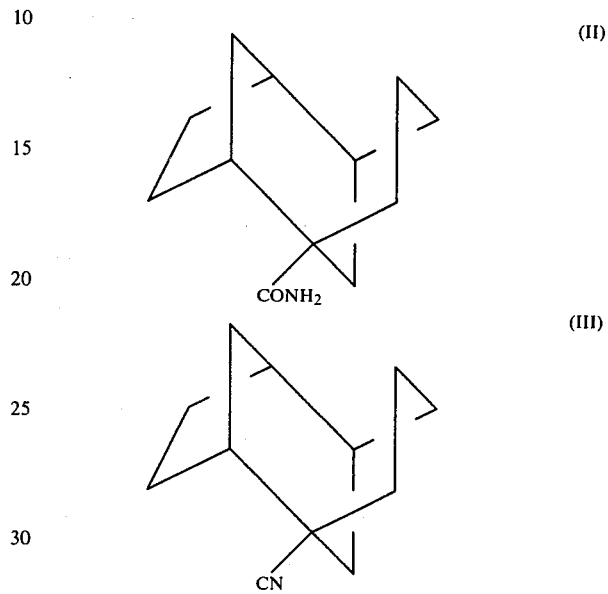

To this reduction reaction are applicable any conventional reaction conditions which are effective in reducing amides and nitriles to their amines. More specifically, the desired compound of the formula (I), 1-aminomethyltricyclo[4.3.1.1$^{2,5}$]undecane, is produced by reducing the compound of the formulae (II) or (III) with lithium aluminum hydride in such a solvent that is inert to both the starting material and the final product, for example, ether, or by subjecting the compound of the formula (III) to catalytic hydrogenation.

1-Aminocarbonyltricyclo[4.3.1.1$^{2,5}$]undecane, which is one of the starting materials of the present invention, is prepared by (1) reacting endo-2-hydroxymethyltricyclo[5.2.1.0$^{2,6}$]decane (disclosed in Japanese Patent Publication No. 1976-13760) with formic acid in the presence of sulfuric acid to produce 1-carboxyltricyclo[4.3.1.1$^{2,5}$]undecane, (2) halogenating the carboxylic acid with a conventional halogenating reagent such as thionyl chloride to product 1-halogenocarbonyltricyclo[4.3.1.1$^{2,5}$]undecane, and (3) then reacting the acid halide with ammonia to produce 1-aminocarbonyltricyclo[4.3.1.1$^{2,5}$]undecane.

1-Cyanotricyclo[4.3.1.1$^{2,5}$]undecane is pepared by dehydrating 1-aminocarbonyltricyclo[4.3.1.1$^{2,5}$]undecane, for example, by contact with thionyl chloride.

The structure of the compound of the formula (I) has been confirmed by its elemental analysis and mass spectrum. As a result of these tests, the compound is recognized to possess one nitrogen atom per molecule and to have a molecular formula of $C_{12}H_{21}N$.

The infrared absorption spectrum of the compound shows peaks at 3500-3100 and 1600 cm$^{-1}$ characteristic of amines and peaks due to the C-H stretching vibration characteristic of the carbon skeleton of the compound of the formula (I). The substitution, position of the amino or cyano group in the starting compound of the formula (II) or (III) is the 1-position, and the isomerization of the carbon skeleton, and the rearrangement of substituents are certainly not expected to take place under the above reaction conditions. The structure of the compound of the formula (I) has been identified by the above analytical data.

Acid-addition salts of the compound of the formula (I) can be easily produced by neutralizing the compound of the formula (I) with acids. Suitable acids to be used include mineral acids such as hydrochloric acid, sulfuric acid, hydrobromic acid, hydroiodic acid, thiosulfuric acid and phosphoric acid; and organic acids such as carboxylic acids, for instance, formic acid, acetic acid, propionic acid, oxalic acid, citric acid and benzoic acid; and sulfonic acids, for instance, benzenesulfonic acid, methansulfonic acid and toluenesulfonic acid. Among these mineral acids particularly preferable are hydrohalogenic acids such as hydrochloric acid, hydrobromic acid and hydroiodic acid.

This invention is hereinafter described more specifically in terms of some Examples which, however, are meant purely to illustrate or explain and not to impose limitations upon the invention. Also given hereinbelow are several Reference Examples which are intended to make clear the advantages of the invention.

EXAMPLE 1

4.5 g (0.023 mole) of 1-aminocarbonyltricyclo[4.3.1.1$^{2,5}$]undecane in 60 ml of tetrahydrofuran was added dropwise with stirring to 1.5 g (0.04 mole) of lithium aluminum hydride in 90 ml of tetrahydrofuran. After the addition is completed, the mixture was stirred under reflux for 1.5 hours. After cooling, 1.5 ml of water, 1.5 ml of a 3 N sodium hydroxide solution and 4.5 ml of water were in turn added to the resulting mixture. The reaction mixture was filtered and then concentrated to obtain 4.0 g of a colorless liquid. This liquid was distilled under reduced pressure to afford 3.2 g (yield: 77.7%) of 1-aminomethyltricyclo[4.3.1.1$^{2,5}$]undecane having a boiling point of 94° C. (0.6 mmHg).

IR (neat): 3500-3100, 3020, 2900, 1600, 1460 cm$^{-1}$.

MS (relative intensity): 179 (M$^+$, 32), 147 (78), 107 (18), 95 (57), 93 (41), 83 (32), 81 (60), 79 (31), 67 (100).

Hydrogen chloride gas was bubbled for 30 minutes into 3.2 g of the thus obtained 1-aminomethyltricyclo[4.3.1.1$^{2,5}$]undecane in 50 ml of dry ether. A precipitate was filtered off, washed with ether and recrystallized from acetone to afford 3.0 g (yield: 80%) of 1-aminomethyltricyclo[4.3.1.1$^{2,5}$]undecane hydrochloride as colorless needles.

Elemental Analysis: as $C_{12}H_{22}NCl$; Calculated: C, 66.80; H, 10.28; N, 6.49; Cl, 16.43%.

Found: C, 66.72; H, 10.32; N, 6.43; Cl, 16.52%.

IR (KBr): 3500, 2900, 1600, 1510 cm$^{-1}$.

MS (relative intensity): 179 (19), 162 (13), 149 (73), 107 (14), 95 (40), 94 (15), 93 (31), 83 (24), 81 (47), 79 (25), 67 (100).

EXAMPLE 2

1.75 g (0.01 mole) of 1-cyanotricyclo[4.3.1.1$^{2,5}$]undecane in 30 ml of dry tetrahydrofuran was added dropwise to 0.45 g of lithium aluminum hydride suspended in tetrahydrofuran. After the addition, the resulting mixture was stirred under reflux for 2 hours. Thereafter, the same procedure was repeated as in Example 1 to afford 1-aminomethyltricyclo[4.3.1.1$^{2,5}$]undecane in a yield of 91%.

REFERENCE EXAMPLE 1

After a monolayer culture of a chick embryo fibroblast cell was incubated in a test tube for 2 to 3 days, a Newcastle disease virus solution having about 128 HAU (hemagglutination unit) and a series of solutions of the test compounds were diluted stepwise. They were incubated at 37° C. for 48 hours, and the virus multiplication was measured with a hemagglutination test. The results obtained are shown in the following table.

| Test compounds | Minimum growth-inhibition concentration (μg/ml) | Minimum cytotoxicity concentration (μg/ml) |
|---|---|---|
| 1-Aminomethyltricyclo-[4.3.1.1$^{2,5}$]undecane hydrochloride (Present compound) | 40 | 40 |
| 1-Aminotricyclo-[4.3.1.1$^{2,5}$]undecane hydrochloride (Control) | 87 | 87 |
| Adamantylamine hydrochloride (Control) | 250 | 250 |

REFERENCE EXAMPLE 2

50 g of endo-2-hydroxymethyltricyclo[5.2.1.0$^{2,6}$]decane dissolved in 200 ml of formic acid was added dropwise with stirring to 400 ml of conc. sulfuric acid over a period of 2.5 hours while the temperature was kept at 0° to 10° C. The mixture was further stirred for 1 hour and allowed to stand. Separated solids were collected by filtration, washed with water and dried to afford 58.2 g (yield: 99.6%) of tricyclo[4.3.1.1$^{2,5}$]undecane-1-carboxylic acid. Recrystallization from n-hexane yielded a white crystal having a melting point of 158.5° to 159.5° C.

Elemental Analysis: as $C_{12}H_{18}O_2$; Calculated: C, 74.19; H, 9.34%.

Found: C, 74.0; H, 9.24%.

IR (KBr): 3300-2700, 1685, 1460, 1405, 1290, 1270 cm$^{-1}$.

Mass Spectrum m/e (relative intensity): 194 (M$^+$, 21), 149 (36), 127 (40), 126 (25), 123 (26), 107 (15), 95 (20).

$^{13}$CNMR (CDCl$_3$, δC): 18.2 (t), 26.2 (t), 26.7 (t+t), 28.1 (t), 30.9 (t), 32.4 (d), 40.3 (d), 42.9 (d), 44.9 (s), 185.6 (s)

REFERENCE EXAMPLE 3

68 ml of thionyl chloride was added dropwise to 46.0 g (0.24 mole) of 1-carboxytricyclo[4.3.1.1$^{2,5}$]undecane dissolved in 200 ml of benzene at room temperature. The resulting mixture was refluxed for 1.5 hours, and excess thionyl chloride and benzene were distilled off under reduced pressure. The residue obtained was fractionally distilled under reduced pressure to afford 47.0 g (yield: 92%) of 1-chlorocarbonyltricyclo[4.3.1.1$^{2,5}$]undecane having a boiling point of 101° C. (1 mmHg).

Elemental Analysis: as $C_{12}H_{17}OCl$; Calculated: C, 67.76; H, 8.06; Cl, 16.67%.

Found: C, 67.61; H, 8.12; Cl, 16.82%.

IR (neat): 3030, 2930, 2875, 2790, 2750 (sh), 1480, 990, 940, 860, 840, 740 cm$^{-1}$.

REFERENCE EXAMPLE 4

10 g (0.047 mole) of 1-chlorocarbonyltricyclo[4.3.1.1$^{2,5}$]undecane was dissolved in 80 ml of anhydrous ether. Under cooling conditions, anhydrous ammonia was bubbled into the mixture for about 15 minutes to deposit a white precipitate. After being filtrated, the precipitate was washed with ether, dried and recrystallized from a solution of benzene and methanol to afford 8.7 g (yield: 96%) of 1-aminocarbonyltricyclo[4.3.1.1$^{2,5}$]undecane having a melting point of 173°–174° C.

Elemental Analysis: as $C_{12}H_{19}NO$; Calculated: C, 74.57; H, 9.91; N, 7.25%.

Found: C, 74.4; H, 9.8; N, 7.4%.

IR (KBr): 3450, 3030, 2925, 1650, 1610 cm$^{-1}$.

Mass Spectrum m/e (relative intensity): 193 (M$^+$, 72), 149 (71), 126 (31), 107 (19), 96 (10), 95 (13), 93 (29), 91 (17), 83 (27), 81 (51).

REFERENCE EXAMPLE 5

A mixture of 3.0 g (0.016 mole) of 1-aminocarbonyltricyclo[4.3.1.1$^{2,5}$]undecane and 12 ml of thionyl chloride was refluxed with stirring for 3.5 hours. After cooling, 20 ml of anhydrous benzene was added to the reaction mixture. The resulting mixture was condensed under reduced pressure, and excess thionyl chloride was distilled off to obtain 2.5 g of a pale yellow crystal. The thus obtained crystal was further purified by sublimation to afford 2.3 g (yield: 84.5%) of 1-cyanotricyclo[4.3.1.1$^{2,5}$]undecane having a melting point of 109°–110° C.

Elemental Analysis: as $C_{12}H_{17}N$ Calculated: C, 82.23; H, 9.78; N, 7.99%.

Found: C, 82.1; H, 9.8; N, 8.1%.

IR (KBr): 3030, 2925, 2225, 1435, 1115, 980 cm$^{-1}$.

Mass Spectrum m/e (relative intensity): 175 (M$^+$, 31), 174 (14), 149 (16), 147 (72), 146 (49), 107 (79), 95 (25), 81 (23), 79 (22), 67 (100).

What is claimed is:

1. 1-Aminomethyltricyclo[4.3.1.1$^{2,5}$]undecane represented by the formula (I) and acid-addition salts thereof.

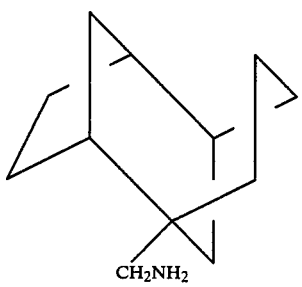

I

2. An acid-addition salt of 1-aminomethyltricyclo[4.3.1.1$^{2,5}$]undecane according to claim 1, wherein the acid-addition salt is a hydrogen halide salt.

* * * * *